United States Patent [19]

Becker

[11] Patent Number: 5,181,907

[45] Date of Patent: Jan. 26, 1993

[54] CANNULA AND METHOD FOR LIPOSUCTION

[76] Inventor: Hilton Becker, 2617 N. Flagler Dr., #304, West Palm Beach, Fla. 33407

[21] Appl. No.: 785,801

[22] Filed: Oct. 31, 1991

Related U.S. Application Data

[63] Continuation-in-part of Ser. No. 496,039, Mar. 20, 1990, abandoned.

[51] Int. Cl.⁵ .................... A61M 1/00; A61B 17/34
[52] U.S. Cl. ...................................... 604/22; 604/902; 604/264; 604/266; 604/268; 606/169
[58] Field of Search ............... 128/768, 759; 604/22, 604/49–51, 266, 268, 280, 264, 902; 606/159, 160, 169, 171

[56] References Cited

U.S. PATENT DOCUMENTS

| | | | |
|---|---|---|---|
| 3,256,885 | 6/1966 | Higgins et al. | 604/268 |
| 3,805,787 | 4/1974 | Banko | 604/22 |
| 3,955,579 | 5/1976 | Bridgman | 604/22 |
| 4,490,138 | 12/1984 | Lipsky et al. | 604/40 |
| 4,536,180 | 8/1985 | Johnson | 604/268 |
| 4,568,332 | 2/1986 | Shippert | 604/119 |
| 4,713,053 | 12/1987 | Lee | 604/49 |
| 4,735,605 | 4/1988 | Swartz | 604/22 |
| 4,815,462 | 3/1989 | Clark | 604/902 |
| 4,816,018 | 3/1989 | Parisi | 604/22 |
| 4,886,491 | 12/1989 | Parisi et al. | 604/22 |
| 5,013,300 | 5/1991 | Williams | 604/902 |
| 5,052,999 | 10/1991 | Klein | 604/49 |

FOREIGN PATENT DOCUMENTS 3804849  9/1988  Fed. Rep. of Germany ...... 606/113

Primary Examiner—Stephen C. Pellegrino
Assistant Examiner—Glenn Dawson
Attorney, Agent, or Firm—Bacon & Thomas

[57] ABSTRACT

A method for removing fatty tissue from a patient includes the steps of inserting an aspirating cannula into the fatty tissue of the body, removing the fatty tissue in the vicinity of an internal layer of the patient's skin and traumatizing the skin adjacent to the area from which fatty tissue is removed. The method is generally carried out by means of an improved aspirating cannula which includes a longitudinally extending tubular member, an opening at one end thereof and a plurality of integrally formed projecting members surrounding the openings. The projecting members are relatively narrow and thin and extend radially outwardly and longitudinally. An annular member which is angularly disposed with respect to the longitudinally projecting member and of similar width and thickness connects the longitudinal members and is effective in breaking down fat tissue without cutting blood vessels or nerves during reciprocal movements of the cannula. The annular member is effective for traumatizing the internal layer of skin adjacent to the area where fatty tissue is removed and causes the skin to shrink in that area.

4 Claims, 2 Drawing Sheets

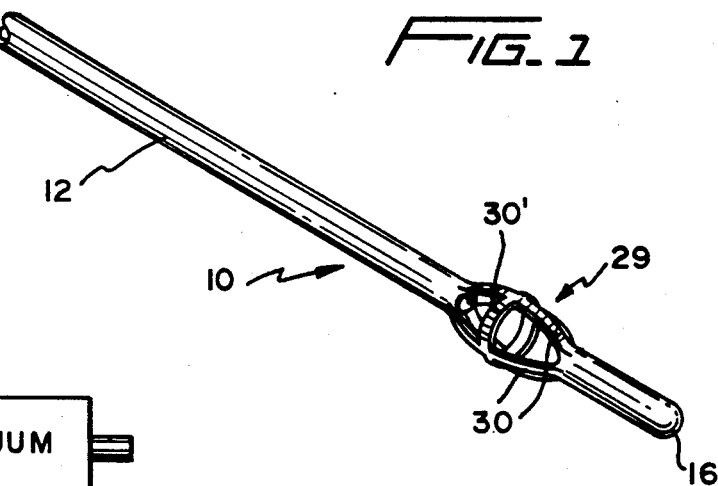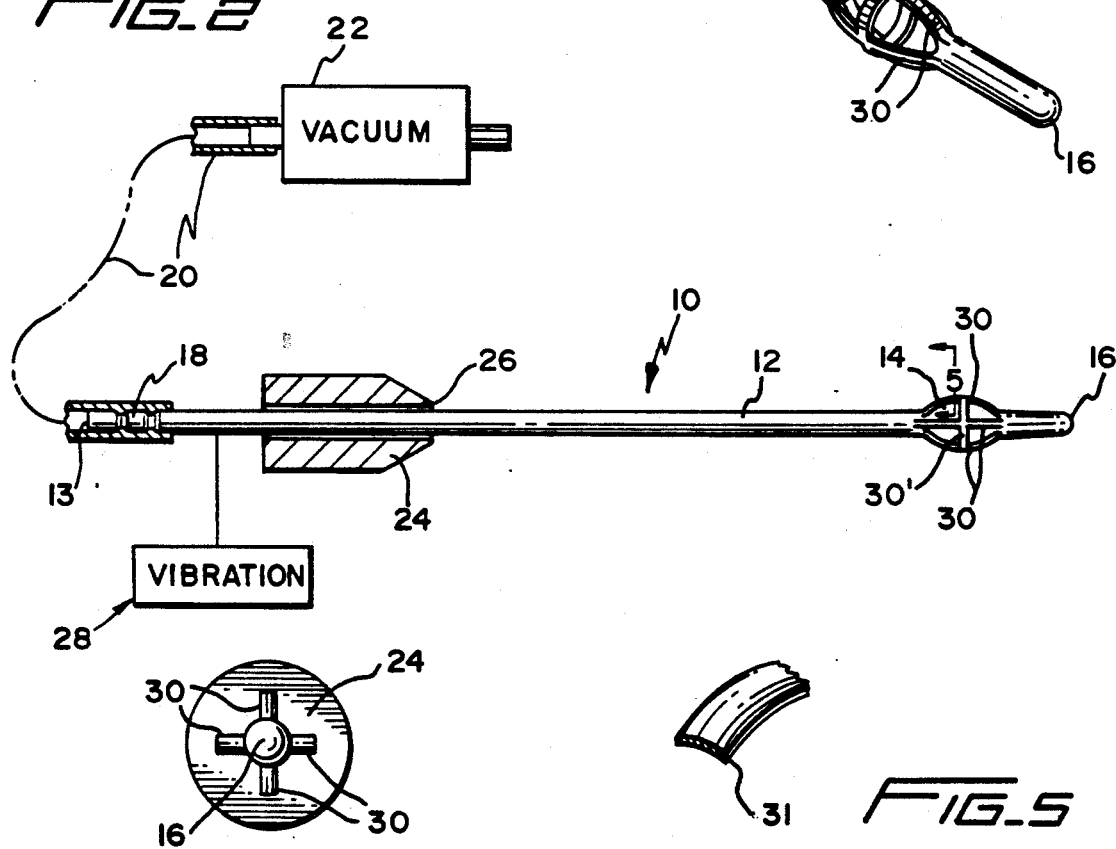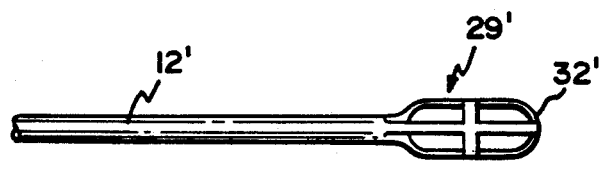

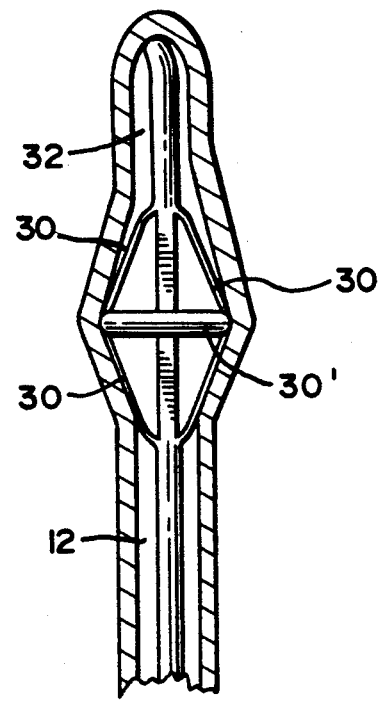
FIG_6
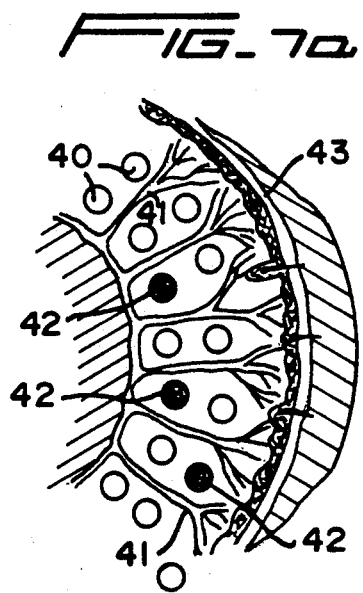
FIG_7a
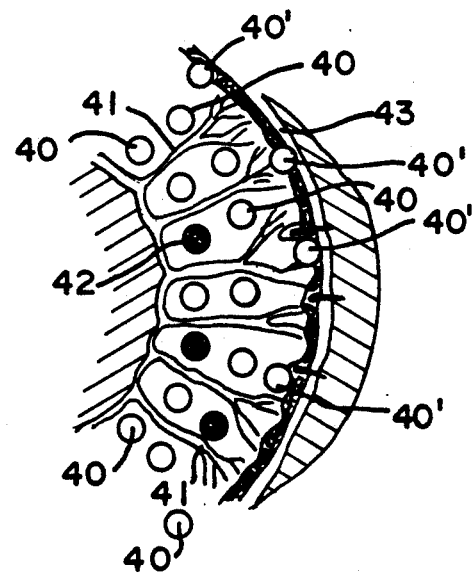
FIG_7b

CANNULA AND METHOD FOR LIPOSUCTION

This application is a continuation-in-part of my earlier U.S. patent application entitled "Cannula for Liposuction," U.S. Ser. No. 07/496,039 which was filed on Mar. 20, 1990, now abandoned.

BACKGROUND OF THE INVENTION

The present invention relates to as aspirating cannula and method for removing unwanted fat from a patient's body and, more particularly, to an improved cannula and method for traumatizing an inner layer of a patient's skin which is in the vicinity of the area of fat removal.

Liposuction has become a widely accepted procedure for removing troublesome localized fat tissue that is unresponsive to diet or exercise. This procedure, which is primarily used by plastic surgeons, is effective in removing excess accumulations of fat from various parts of the body. For example, regions of the body frequently treated include the waist (love handles), buttocks, thighs (saddle bag deforming), inner upper thighs, knees, ankles, lower legs, upper arms, etc.

The removal of excess fat tissue by liposuction is typically accomplished by inserting a narrow metal tube through a small incision in the skin and applying a vacuum suction. The tube has a round end and a small opening along the side close to the tip. The surgeon typically massages the flesh in the area of the opening in the cannula and at the same time thrusts the cannula forward and backward within the layer of fat. This in and out movement shears off fat tissue particles which are drawn into the tube and out of the body by a vacuum. Thus, the surgeon creates a sponge-like effect within the tissue by developing numerous interconnected and closely related tunnels. Typically, twenty to thirty tunnels are made so that the fullness, firmness and size of an area is reduced. Thus the collapse and shrinkage in the treated area creates a more enhanced contour.

The surgical procedure described above is traumatic and is usually accompanied by bruising in the treated area. This bruising may be quite extensive and is due to the disruption of small blood vessels which are attached to the fat globules. The blunt end of the cannula pushes the larger blood vessels and nerves out of the way. Nevertheless, there is a demand for an improved cannula that will minimize, insofar as possible, disruption of the blood vessels and nerves.

Many surgeons who use liposuction find that the procedure is physically demanding and tiring. Consequently, there is a need for an improved cannula which will not only reduce the trauma to the patient, but also the need for physical strength by a surgeon in forcing the cannula through the fatty tissue. There is also a demand for an improved cannula which would enable a physician to speed up the procedure, facilitate the quick removal of fatty tissue and at the same time make it easier for the surgeon to more accurately select or position the tunnels being formed in a layer of fatty tissue.

It is presently believed that an improved cannula and the novel combination of an improved cannula, source of vacuum and vibration means will overcome many of the disadvantages of the prior art devices. For example, it is presently believed that the improved cannulae which are disclosed herein will reduce a surgeon's effort in performing liposuction, enable the surgeon to accurately position the cannula in removing fat from prescribed areas, minimize the likelihood of tracking, i.e., forming imperfections by removing fat from the inner surface of a patient's skin and at the same time reduce the trauma to a patient by minimizing damage to the patient's blood vessels and nerves. It is also believed that the improved cannula disclosed herein can be manufactured and sold at a competitive price, i.e., without a significant increase in cost as compared to conventional cannulae.

BRIEF SUMMARY OF THE INVENTION

Briefly, a method for removing unwanted fat from a patient's body in accordance with the present invention includes the step of inserting an aspirating cannula into the fatty tissue in the body of a patient in an area which is between the flesh or internal layer of skin and the muscle. Longitudinal passageways are then formed by forcing the aspirating cannula through the fatty tissue to thereby break down the fat cells which are then removed by the aspirating cannula. In performing the surgical procedure, the fatty tissue which is adjacent to the inner layer of skin is removed thereby traumatizing the inner layer of skin. This causes the skin to shrink or contract which, in some cases, eliminates a need to remove excess skin after removal of the fatty tissue.

In essence, an improved cannula according to the present invention comprises an elongated tube having openings at each end thereof. A proximal end of the tube is adapted for a connection to a source of vacuum while the distal end is adapted for insertion through an incision into the fatty tissue of a patient's body. The distal end defines an opening and a closed (preferably bullet-shaped) portion forwardly of the opening. The distal end also includes means such as a plurality of radially outwardly projecting and longitudinally extending members and an angularly disposed annular cross-member for breaking down the fatty tissue for aspiration thereof. The outwardly projecting members may also serve to maintain that portion of the cannula where there is a maximum vacuum, i.e., the area of the tube which is immediately adjacent the opening, at a discrete distance from the inner surface of a patient's skin, while the annular cross-member which is preferably transverse of the outwardly projecting and longitudinally extending member can be used to traumatize an internal layer of skin and adjacent to the area of fat removal.

The invention also contemplates a novel combination of an improved cannula as defined above, a source of vacuum and a means for vibrating the distal end of the cannula. And in a preferred embodiment, grip means are provided which isolate the vibrating cannula from the surgeon's hand while the vibrating means oscillates the tip of the cannula within the ultrasonic range.

BRIEF DESCRIPTION OF THE DRAWINGS

The improved cannula according to the present invention will now be described in conjunction with the accompanying drawings wherein:

FIG. 1 is a perspective view illustrating a distal end portion of a cannula according to a first embodiment of the invention;

FIG. 2 is a schematic side elevational view of a cannula according to the preferred embodiment of the invention as used in connection with vibrating means and a source of vacuum;

FIG. 2a is an end view of the cannula shown in FIGS. 1 and 2;

FIG. 3 is a side elevational view of the distal portion of a cannula according to a second embodiment of the invention;

FIG. 4 is an end view of the distal portion of the cannula shown in FIG. 3;

FIG. 5 is a perspective view of the distal portion of the cannula shown in FIG. 2;

FIG. 6 is a side elevational view of a distal end portion of a cannula according to a presently preferred embodiment of the invention;

FIG. 7a is a perspective view showing a schematic cross-section of a patient's fatty tissue, skin and muscle with tunnels formed in the fatty tissue by liposuction performed in accordance with conventional practices; and FIG. 7b is a perspective view showing a schematic cross-section of a patient's anatomy as shown in FIG. 7 but including areas of subdermal fat resection.

DETAILED DESCRIPTION OF THE PREFERRED EMBODIMENT

Traditionally, liposuction has been performed using a blunt cannula to create a series of tunnels in the deeper layer of the fatty tissue. To be more specific, the subdermal layer of fat is preserved to avoid rippling or depressions in the skin. However, it has now been found that depressions can be advantageously formed in certain areas of the body. For example, it may be desirable to form a deeper buttock crease or achieve a "hollow" neck following a submental lipectomy or creating inframammary crease.

It now appears that the skin actually contracts into any such depressions. For example, skin contraction is also seen following subcutaneous mastectomies where thin flaps have been raised. For this reason, an improved cannula in accordance with the present invention was developed to specifically resect the subdermal fat. It is believed that subdermal fat resection enhances skin contraction, thus facilitating contouring of the skin over the underlying tissues.

With reference now to the figures and more particularly to FIGS. 1, 2 and 2a, an improved cannula 10 according to a first embodiment of the invention includes a relatively narrow tube 12 with openings 13 and 14 at each end thereof. The tube 12 has a smoothly-contoured outer surface which is substantially symmetrical about the longitudinal axis of cannula 10 and which might be defined as an elongated right circular cylinder. This tube 12 is preferably made of surgical or stainless steel but may, in come cases, be made of a hard plastic such as polycarbonate. The tube 12 may also be slightly tapered toward the distal, i.e., smaller, end. The cannula 10 may be of almost any length from about 5 cm to 40 cm, depending upon its intended use. For example, a cannula of about 30 cm might be preferred for large areas such as the buttocks, while a small 5 cm cannula would be preferred for facial surgery. The diameter of the tube 12 is also variable and may vary within the range of 5 to 25 mm and is preferably slightly tapered with the smaller diameter at the distal end 16 of the cannula 10.

The distal end 16 is rounded or bullet-shaped and may approximate a hemisphere. In essence, the end 16 defines a smoothly-contoured outer surface which is substantially symmetrical about its longitudinal axis. This rounded or bullet-shaped end 16 preferable extends forwardly of the cage-like structure 29 for a distance which is about equal to ½ to 1 times its diameter and is effective in pushing larger blood vessels and nerves to one side in order to reduce trauma to the patient, loss of feeling and excessive loss of blood.

A proximal end 18 of tube 12 may be knurled or include a number of indentations or the like and is thus adapted to have a rubber hose 20 slipped thereon. The hose 20 connects the cannula 10 to a source of vacuum shown schematically at 22. A grip means or handle 24 is provided near the proximal end 18 and may be made of hard plastic of the like. The handle 24 may be contoured to fit the surgeon's hand and may be separated from tube 12 by damping means 26. The damping means 26 may be of rubber or other elastomer which is used to isolate the surgeon's hand from vibration when it is desired to vibrate the cannula during a surgical procedure. In such procedures, the vibration is generated by a source of vibration 28.

In one embodiment of the invention, the distal end 16 of the tube 12 is vibrated ultrasonically by means of a piezo-electric crystal (not shown). For example, when an electric current is applied to the piezo-electric crystal, which may be mounted within the handle 24 or fixed to the tube 12, the crystal vibrates back and forth at approximately 35,000 cycles per second. This causes the distal end 16 to vibrate longitudinally. It is believed that the major force or amplitude will be concentrated at member 30 which will be described in more detail hereinafter.

An important aspect of the present invention resides in a cage-like structure 29. This cage-like structure 29 includes a plurality, at least three and preferably four radially outwardly projecting and longitudinally extending members 30 which are equally spaced circumferentially about a forward end of the cannula 10. The members 30 are preferably formed as an integral part of the forward portion of the tube 12 and connect the middle portion of tube 12 to the bullet-shaped end 16 which is also preferably formed as an integral part of tube 12. As illustrated in FIG. 5, a member 30' forms an additional ring on the widest portion of the outwardly projecting member 30 and is believed to aid in breaking down the fat cells. For example, as illustrated the ring member 30' is about midway along the longitudinal members but also where the distance between opposite longitudinal members is greatest.

The members 30 each include rounded leading and trailing edges 31 as illustrated more clearly in FIG. 4. Thus, when the cannula is thrust in a forward and backward direction with a slight twisting action, the leading edges 30 will break down the fat cells or tend to remove fat particles from the surrounding tissue with minimal damage to blood vessels and nerves and at the same time minimize the physical effort required by the surgeon. And, when these members are vibrated in the manner described above, the required work will be further reduced.

The outwardly extending portions 30 will also keep the area immediately adjacent opening 14 away from the inner surface of a patient's skin and thus reduce the likelihood of producing unsightly tracks in a patient's skin.

In a preferred embodiment of the inventions as illustrated in FIG. 6, the cage-like structure 29 is formed as an integral part of tube 12 and comprises four equally spaced outwardly projecting and longitudinally extending members 30 which are circumferentially or equiangularly spaced about the longitudinal axis of the cannula and an annular ring 30' which connects the longitudinal member 30 at the widest points, i.e., at the greatest distance from an opposite member to form a cage-like structure. Thus, the cannula features a round profile with vertical and horizontal projections. The vertical (longitudinal) projections tend to push nerves and vessels out of the suction field while the horizontal (lateral) projection provides maximum dissection of tissues. This design is presently considered ideal for resection of fat, scar and breast and certain lymphadematous tissue. Each of the members 30 are relatively narrow, i.e., about 1/16" to about ¼" and have a relatively flat portion which extends longitudinally for a distance of ¾ to 1½ times the diameter of tube 12 taken in the second immediately adjacent the forward or rear part of the cage-like structure 29. The cage-like structure 29 also extends outwardly from the adjacent surface of tube 12 by as slight distance, e.g., about one-eighth of the diameter of tube 12. Thus, a typical cannula might have an outside diameter of tube 12 equal to about 0.5 inches, the length and width of each of members 30 of about ⅝" and ¼", respectively, and a thickness (the same as tube 12) of about 0.020 to 0.040 inches. In this case, the distance between opposite members 30 of the cage-like structure 29 would be about 0.625 inches.

A second embodiment of the invention is illustrated in FIGS. 3 and 3a. As illustrated therein, a longitudinally extending tube 12' includes a cage-like structure 29a which includes a plurality of integrally formed outwardly projecting longitudinally extending members 30a. However, in the second embodiment, the outwardly extending members also form a bullet-shaped forward end 32a of the cannula.

The improved cannula, according to the present invention, may be used in the same manner as conventional cannulae. For example, in a typical lipectomy, a region to be suctioned is selected and anaesthesia, either general or local, given to a patient in a manner which will be well understood by a plastic surgeon of ordinary skill in the art.

An incision of from 5 to 20 mm in length is made and the distal end 16 of cannula 10 is inserted through the incision and into the fatty tissue. The vacuum source and source of vibration are activated to produce a negative pressure at from about 0.3 to 1.5 atmospheres and a vibration of about 35,000 cycles per second. The vibration may, for example, be produced by equipment which is available from Ultrovac, Inc. of 12344 Oakknoll Road, Poway, Calif. 92064.

When the cannula is in place and the vacuum and vibration activated, the surgeon gently massages the region to be treated and thrusts the cannula into the layer of fatty tissue with or without a slight twisting motion. In practice, the cannula is thrust into the fatty tissue at a relatively deep level to thereby break up the fatty tissue for aspiration through the cannula.

As illustrated in FIGS. 7a and 7b, it is desirable to leave small interleaving areas of tissue intact between the tunnels 40 and to preserve the nerves 41 and larger blood vessels 42 that nourish the overlying skin 43. As illustrated in FIG. 7a, care has been taken to avoid resection of the subderminal fat. However, as illustrated in FIG. 7b, the member 30' has been used to facilitate subdermal fat resection. For example, the tunnels 40' are formed adjacent the internal layer of a patient's skin which has been found to cause contraction of the skin in that area. The skin contraction facilitates contouring of the skin over the underlying tissue.

The above technique has been found to be most successful in performing liposuction in the neck and also for rapidly resecting in the pendulous abdomen and breast.

It is believed that the outwardly projecting members 30 and the slight twisting motion of the cannula may further reduce the trauma to the patient and work of the surgeon by eliminating the physical tearing of the tissue. It is also believed that the design of the members 30, i.e., the relatively thin member with rounded edges, minimizes the damage to the small blood vessels and nerves. And, the addition of the ultrasonic vibration should further reduce the work and trauma. Therefore, the operating procedure may be accomplished more accurately and more quickly which means that the patient will have less time under an anaesthetic. In addition, it is believed that the cannula disclosed herein tends to break up the fat or facilitates the injection of such fat at another location.

Other standardized procedures for liposuction are then followed.

While the invention has been described in connection with its preferred embodiment, it should be understood that changes and modifications can be made without departing from the scope of the appended claims.

What is claimed is:

1. The combination of a cannula for aspirating fat from a patient comprising an elongated tubular member having proximal and distal ends wherein said distal end is adapted for insertion into a patient's fatty tissue through an incision in the patient's body and for being reciprocally inserted into and out of the fatty tissue by a surgeon, said elongated tubular member defining an opening near its distal end, said opening encompassing essentially the entire circumference of the tubular member and means forming a closed rounded or bullet-shaped end portion forwardly of the opening for facilitating its insertion into fatty tissue and passage therethrough, said tubular member further defining means including a plurality of longitudinally extending members projecting radially outwardly from the opening beyond the surface of said tubular member and extending longitudinally in the direction of said tubular member and connecting said tubular member to said bullet-shaped end portion, said longitudinally extending members having relatively thin rounded edges which are adapted to break down fat cells without damaging nerves and/or blood vessels and an annular member transverse of and connecting said longitudinal members for breaking down the fatty tissue and for preventing the area immediately adjacent the opening from coming into contact with the inner surface of a patient's skin, said elongated tubular members having a smoothly-contoured outer surface which is substantially symmetrical about its longitudinal axis between said proximal end and said opening, and vacuum means connected to the proximal end of said tubular member so that fat tissue, which is broken down by reciprocating movements of the cannula, is drawn out of the patient and through the tubular member for disposal thereof.

2. The combination according to claim 1 in which said plurality of radially outwardly and longitudinally extending members are equally spaced about the circumference of said cannula.

3. The combination according to claim 2 in which said annular member connects said longitudinal members at points where the distance between opposite longitudinal members is greatest.

4. The combination according to claim 3 in which said closed rounded end portion of said cannula defines a hemispherical shape.

* * * * *